(12) United States Patent
Anthony

(10) Patent No.: US 10,661,040 B2
(45) Date of Patent: May 26, 2020

(54) MEDICAL SUPPORT FOR DELIVERY OF A TREATMENT TO THE NOSE

(71) Applicants: TOMTEC NV, Kapellen (BE); ANTHONY MEDICAL & MARINE TECHNOLOGIES BVBA, Kapellen (BE)

(72) Inventor: Jean-Michel Anthony, Kapellen (BE)

(73) Assignees: Reginald Nieberding, Kapellen (BE); Tom Ponnet, Schoten (BE); Jean-Michel Anthony, Kapellen (BE)

( * ) Notice: Subject to any disclaimer, the term of this patent is extended or adjusted under 35 U.S.C. 154(b) by 1321 days.

(21) Appl. No.: 14/767,384

(22) PCT Filed: Feb. 14, 2014

(86) PCT No.: PCT/EP2014/052901
§ 371 (c)(1),
(2) Date: Aug. 12, 2015

(87) PCT Pub. No.: WO2014/125066
PCT Pub. Date: Aug. 21, 2014

(65) Prior Publication Data
US 2015/0374945 A1    Dec. 31, 2015

(30) Foreign Application Priority Data
Feb. 14, 2013   (EP) .................................... 13155287

(51) Int. Cl.
*A61M 16/06*    (2006.01)
*B32B 5/24*    (2006.01)
(Continued)

(52) U.S. Cl.
CPC ...... *A61M 16/0683* (2013.01); *A61J 15/0003* (2013.01); *A61J 15/0053* (2013.01);
(Continued)

(58) Field of Classification Search
CPC ...... A61M 2016/0661; A61M 16/0683; A61M 2207/00; B29C 51/02; B29C 51/145;
(Continued)

(56) References Cited

U.S. PATENT DOCUMENTS

| 2004/0079374 A1 | 4/2004 | Thornton |
| 2006/0005837 A1 | 1/2006 | Thornton |

(Continued)

FOREIGN PATENT DOCUMENTS

| DE | 19846686 A1 | 7/1999 |
| EP | 1186314 A2 | 3/2002 |

(Continued)

*Primary Examiner* — Timothy A Stanis
*Assistant Examiner* — Victoria Murphy
(74) *Attorney, Agent, or Firm* — Clark & Elbing LLP; Susan M. Michaud

(57) ABSTRACT

The present invention provides a wearable medical support for delivery of a treatment to the nose of a subject comprising: a nose mask formed from a heat moldable sheet of thermoplastic material, said nose mask comprises an aperture dimensioned to fit the nose of the subject, said aperture is flanked by two flaps whereby each flap is configured to be in contact with at least part of a lateral side of the nose; and a device configured to close fit said aperture, said device is provided at one end with an opening for receiving the nose and at the other end with at least one coupling suitable to be connected to one or more tubes for delivery of the treatment to the nose. The present invention further provides a sheet of heat moldable thermoplastic material for molding a mask directly on a subject's nose.

17 Claims, 10 Drawing Sheets

(51) Int. Cl.
*B32B 3/26* (2006.01)
*B32B 5/04* (2006.01)
*B32B 27/12* (2006.01)
*B29C 51/14* (2006.01)
*B29C 51/00* (2006.01)
*B32B 7/14* (2006.01)
*B32B 5/02* (2006.01)
*B32B 27/40* (2006.01)
*A61J 15/00* (2006.01)
*B29C 51/02* (2006.01)
*B29K 33/04* (2006.01)
*B29L 9/00* (2006.01)
*B29L 31/00* (2006.01)

(52) U.S. Cl.
CPC ......... *A61M 16/0666* (2013.01); *B29C 51/00* (2013.01); *B29C 51/002* (2013.01); *B29C 51/02* (2013.01); *B29C 51/145* (2013.01); *B32B 3/266* (2013.01); *B32B 5/024* (2013.01); *B32B 5/026* (2013.01); *B32B 5/04* (2013.01); *B32B 5/245* (2013.01); *B32B 7/14* (2013.01); *B32B 27/12* (2013.01); *B32B 27/40* (2013.01); *A61M 2016/0661* (2013.01); *A61M 2205/0205* (2013.01); *A61M 2205/0216* (2013.01); *A61M 2205/7527* (2013.01); *A61M 2207/00* (2013.01); *B29K 2033/04* (2013.01); *B29K 2995/0037* (2013.01); *B29L 2009/00* (2013.01); *B29L 2031/753* (2013.01); *B32B 2255/02* (2013.01); *B32B 2255/102* (2013.01); *B32B 2255/26* (2013.01); *B32B 2262/0261* (2013.01); *B32B 2262/0276* (2013.01); *B32B 2262/06* (2013.01); *B32B 2266/025* (2013.01); *B32B 2266/0228* (2013.01); *B32B 2266/0235* (2013.01); *B32B 2266/0242* (2013.01); *B32B 2266/0278* (2013.01); *B32B 2266/08* (2013.01); *B32B 2270/00* (2013.01); *B32B 2307/51* (2013.01); *B32B 2307/728* (2013.01); *B32B 2571/00* (2013.01)

(58) Field of Classification Search
CPC ......... B29C 51/00; B32B 5/245; B32B 3/266; B32B 2307/728
See application file for complete search history.

(56) References Cited

U.S. PATENT DOCUMENTS

| 2006/0096598 | A1 | 5/2006 | Ho et al. |
| 2009/0267261 | A1 | 10/2009 | Mark |
| 2011/0132375 | A1 | 6/2011 | Thornton |
| 2012/0055485 | A1 | 3/2012 | Anthony |
| 2012/0204870 | A1* | 8/2012 | McAuley ............. A61M 16/06 128/203.12 |
| 2014/0158136 | A1* | 6/2014 | Romagnoli ....... A61M 16/0683 128/206.24 |

FOREIGN PATENT DOCUMENTS

WO WO-2010125074 A1 * 11/2010 ............. A61M 16/06
WO WO 2013/001083 A1 1/2013

* cited by examiner

MEDICAL SUPPORT FOR DELIVERY OF A TREATMENT TO THE NOSE

CROSS-REFERENCE TO RELATED APPLICATIONS

This application is the U.S. National Phase under 35 U.S.C. § 371 of International Application PCT/EP2014/052901, filed Feb. 14, 2014, which claims priority to EP 13155287.9, filed Feb. 14, 2013.

FIELD OF THE INVENTION

The present invention relates to the field of a wearable support for the delivery of a treatment through the nose of a subject. In particular, it concerns a support that can be worn for the treatment of sleep apnea, or for supporting a catheter providing air to the lungs or liquid nutrition to the stomach.

BACKGROUND

A variety of supports are known in the art that may be worn by a subject and which secure a tube for the delivery of a treatment (e.g. a liquid, a gas) through the nose.

The most common supports are respiratory masks, which are triangular in shape to compliment the nose, and seal against the skin of the subject, as described for instance, in U.S. 2006/0096598. A disadvantage of such masks is the weight and the low level of comfort they afford the wearer. Because they seal using a triangular facial component, pressure is applied to the skin in a concentrated region along the triangle edges. They result in unseemly pressure marks to the skin of the wearer after use. Such masks may be worn only for limited period of time without the risk of adverse reaction. They are unsuitable for wearing at night, as required by sufferers of sleep apnea for long and repeated periods.

US 2006/0005837 discloses a custom fitted mask configured for coupling to an external gas supply system. The mask comprises a first sheet of deformable material that has been deformed against a user's face surrounding the user's nostrils while the first sheet is in a deformable state to conform substantially optimally to the user's unique facial features. The mask further comprises a fitting adapted for coupling to the external gas supply system; and a second sheet of deformable material configured around the fitting. The second sheet is applied against the fitting while the second sheet is in a deformable state such that the fitting is positioned between the first and second sheets, a contact portion of the second sheet conforming substantially optimally to a contact portion of the first sheet and being bonded to the contact portion of the first sheet. US 2004/0079374 discloses a custom fitted mask, comprising a first thin sheet of deformable material that has been formed and fitted to a first portion of a user's face surrounding the user's nostrils. The mask comprises fittings that have been inserted for coupling the mask to an external gas supply system. In these masks, the fitting is permanently fixed to the mask. This is disadvantageous as the mask has to be discarded as soon as the fitting is damaged (after a multiple use and/or a miss-use for instance).

Another type of masks is described in WO 2010/125074. Said mask is a heat moldable nose mask, having a longitudinal direction, formed from a sheet of thermoplastic material configured for individual molding across at least part of the cheek bones of the subject. The mask comprises a nose aperture dimensioned to fit the nose of the subject, and a fixture for a strap at each opposing longitudinal end of the mask. These types of masks are also prone to dislodging especially the wearer is sleeping. Moreover, the mask covers a large surface of the face thereby providing the wearer with a low level of comfort.

The aim of the present invention is to provide a solution to overcome at least part of the above mentioned disadvantages. The invention thereto aims to provide an improved wearable medical support and an improved mask for treatment delivery to the nose. In particular, the invention provides a wearable medical support and a mask as described in claim 1. Further details of the invention are provided by the dependent claims.

SUMMARY

In a first aspect, the present invention provides a sheet of heat moldable thermoplastic material for molding a mask directly on a subject's nose via thermoforming, said sheet is initially substantially flat and comprises one or more fixtures for attachment to a strap and a nose opening, said nose opening has an substantially inverted T shape comprising a slit which extends to a lower opening, which opening is substantially perpendicular to the slit, whereby the slit delimits two flanking flaps. After thermoforming on a subject's nose, said sheet extends across at least part of the cheek bones of the subject, whereby the nose bridge protrudes at least partially through said slit, the nose nostrils protrude at least partially through said lower opening; and each lateral side of the nose is at least partially covered by a flanking flap. After thermoforming of the sheet on a subject's nose, a nose mask is obtained.

In a second aspect, the present invention provides a wearable medical support for delivery of a treatment to the nose of a subject comprising:
  a nose mask formed from a heat moldable sheet of thermoplastic material as described above, said nose mask comprises an aperture dimensioned to fit the nose of the subject, said aperture is flanked by two flaps whereby each flap is configured to be in contact with at least part of a lateral side of the nose,
  a device configured to close fit said aperture, said device is suitable to at least partially pass through the nose aperture of the nose mask and is provided at one end with an opening for receiving the nose and at the other end with at least one coupling suitable to be connected to one or more tubes for delivery of the treatment to the nose.

In a third aspect, the present invention provides a kit for delivery of a treatment to the nose of a subject comprising: a sheet of thermoplastic material as described above for molding a nose mask having an aperture dimensioned to fit the nose of the subject, a device configured to close fit said aperture as described above and at least one pressurizing means for applying a pressure on the sheet of thermoplastic material during the molding process.

In a fourth aspect, the present invention provides for the use of a kit according to the invention for molding directly a nose mask on a subject's nose for delivery of a treatment to the nose of said subject.

The sheet of heat moldable thermoplastic material, the wearable medical support and the kit of the present invention present several advantages. The sheet nose mask is easily obtainable by molding and is personalized as it's molded directly on the face, more in particular on the nose of the subject. The presence of flaps on the lateral sides of the nose provides more stability to the mask thereby reducing the chances of being dislodged. Moreover, the surface of the face covered by the mask can be reduced as the flaps provide good stability to the mask which provides more comfort to the wearer.

Another advantage is the dismountable coupling of the device and the nose mask which allows a better cleaning of the device and/or the nose mask thereby insuring high level of hygiene to the wearer. Furthermore, in case of damage, only the damaged part, the device and/or the nose mask, needs to be replaced by a new one.

DETAILED DESCRIPTION OF THE INVENTION

The present invention relates to a sheet of heat moldable thermoplastic material for molding a mask directly on a subject's nose. The invention further relates to a wearable medical support and a kit for the delivery of a treatment to the nose of a subject.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The terms "wearer" and "subject" are used herein as synonyms and refer to the person using the support of the present invention.

The terms "distal" and "proximal" are used through the specification, and are terms generally understood in the field to mean towards (proximal) or away (distal) from a reference point. For instance, "proximal" or "proximal side" of the wearer means towards and close to the wearer. Conversely, "distal" or "distal side" of the wearer means away from the wearer.

The expression "lateral side of a nose" is used herein to refer to the nose wings of a human.

By "treatment" it is referred herein to a fluid or to a gas.

Figure 1:
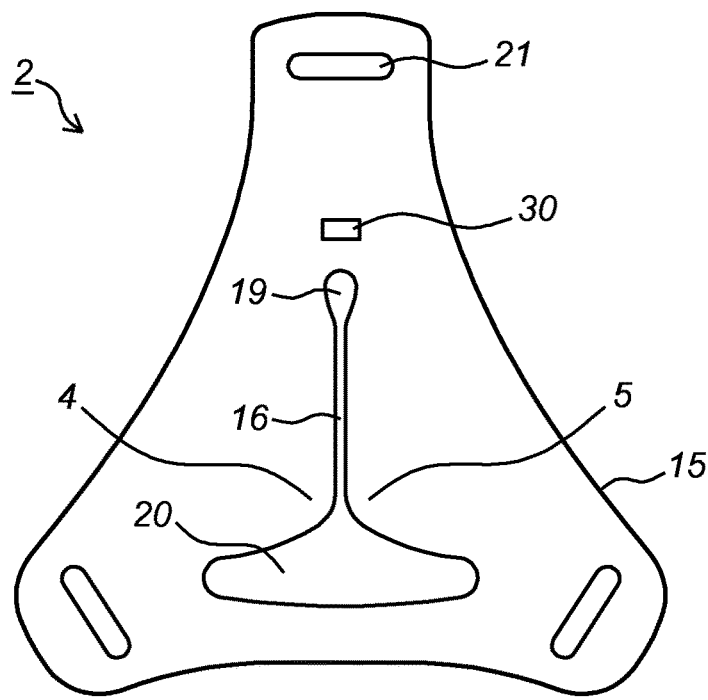
FIG. 1 shows a sheet of heat moldable thermoplastic material according to the present invention. The sheet is in a non-molded state.
Figure 2:
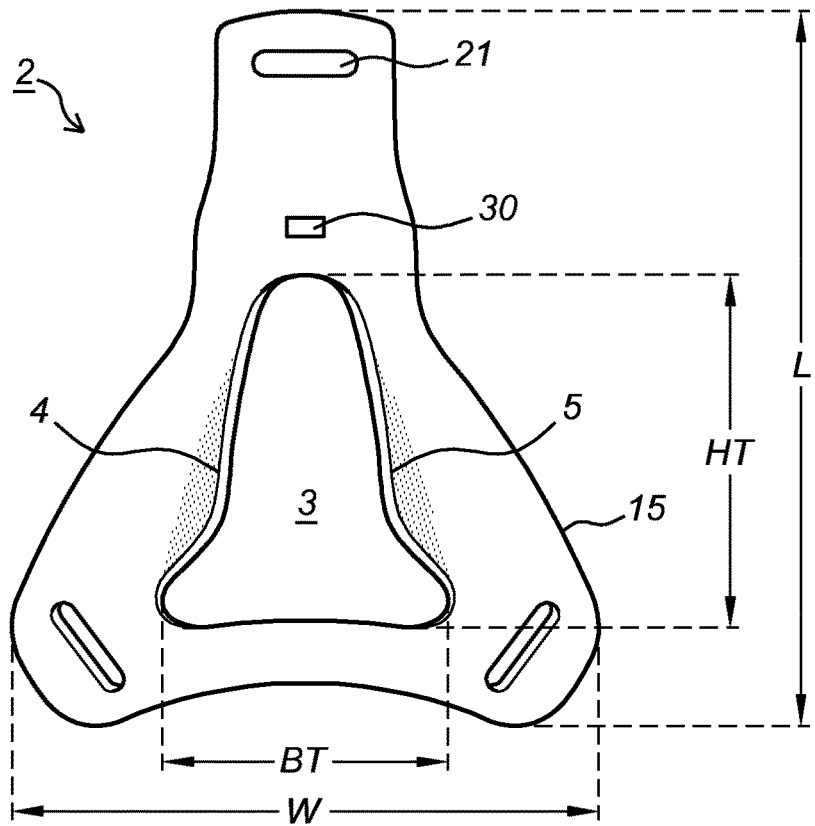
FIG. 2 shows a nose mask according to the present invention. The mask is obtained by molding the sheet of heat moldable thermoplastic material shown in FIG. 1 on a subject's nose.

In a first aspect, the present invention provides a sheet of heat moldable thermoplastic material 15 (FIG. 1) for molding a mask directly on a subject's nose via thermoforming, said sheet is initially substantially flat and comprises one or more fixtures 21 for attachment to a strap and a nose opening, said nose opening has an substantially inverted T shape comprising a slit 16 which extends to a lower opening 20, which opening 20 is substantially extending perpendicular to the slit 16, whereby the slit 16 delimits two flanking flaps 4,5. After thermoforming on a subject's nose, said sheet extends across at least part of the cheek bones of the subject, whereby the nose bridge protrudes at least partially through said slit 16, the nose nostrils protrude at least partially through said lower opening 20; and each lateral side of the nose is at least partially covered by a flanking flap 4,5 (FIG. 2). In a preferred embodiment, the slit 16 of the sheet of heat moldable thermoplastic material 15 is also extending to an upper opening 19 as shown in FIG. 1. The presence of said upper opening 19 is optional.

In a preferred embodiment, the length of the slit is such as at least part of the nose bridge is covered by the thermoformed sheet. In this case, the flaps of the mask will be connected to each other by said thermoformed sheet covering part of the nose bridge. The length of the slit 16 is of at least 1 mm, preferably at least 3 mm, more preferably at least 5 mm, most preferably at least 10 mm, even most preferably at least 20 mm. The length of slit 16 is at most 4 cm, preferably at most 3 cm, more preferably at most 2.5 cm, most preferably 2 cm. The length of the slit 16 can be any value comprises in between the above mentioned values.

In a preferred embodiment, the heat moldable thermoplastic material 15 is initially partially thermoformed.

Figure 3:
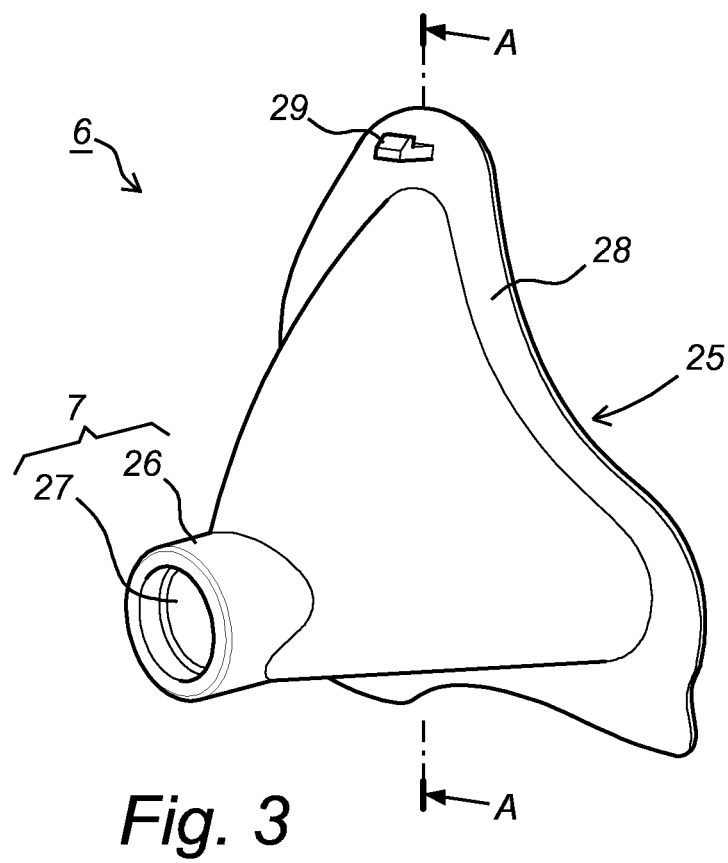
FIG. 3 shows a device configured to close fit the aperture of the nose mask.

In a second aspect, the present invention provides a wearable medical support 1 formed from a heat moldable nose mask 2 (FIG. 2) comprising an aperture 3 for the nose and a removable device 6 (FIG. 3) configured to close fit said aperture 3. The mask further comprises fixtures 21 for attachment to a strap (FIG. 2), and the device comprises a coupling 7 for attachment of one or more tubes for delivery of a treatment to the nose (FIG. 3).

The nose mask 2 element of the support 1 is obtained by direct thermoforming the sheet of heat moldable thermoplastic material 15 on a subject's face, meaning it may be adapted to the contours of the face, more specifically of the nose, so providing a comfort fit enabling it to be worn for extended periods. Where the support 1 is used for delivery of pressurized air, for instance, in the treatment of sleep apnea, the individual fit also provides a partial sealing function. The skin contact or facing surface of the mask 2 may be lined with a softened material such as a felt, neoprene, open cell foam or knitted material. The use of a softened material not only provides a pleasant feeling against the skin, but also allows a partial flow of circulating air across rather than through the mask, thereby reducing the buildup of perspiration and heat below the mask. The mask 2 is particularly suitable for wearing at night without discomfort, and so may be utilized in the treatment of sleep apnea when the treatment delivered to the noise is air. Equally, the support can be used as an attachment point for a feeding tube or breathing tube inserted through the nose. The support 1 is washable.

Figure 10A:
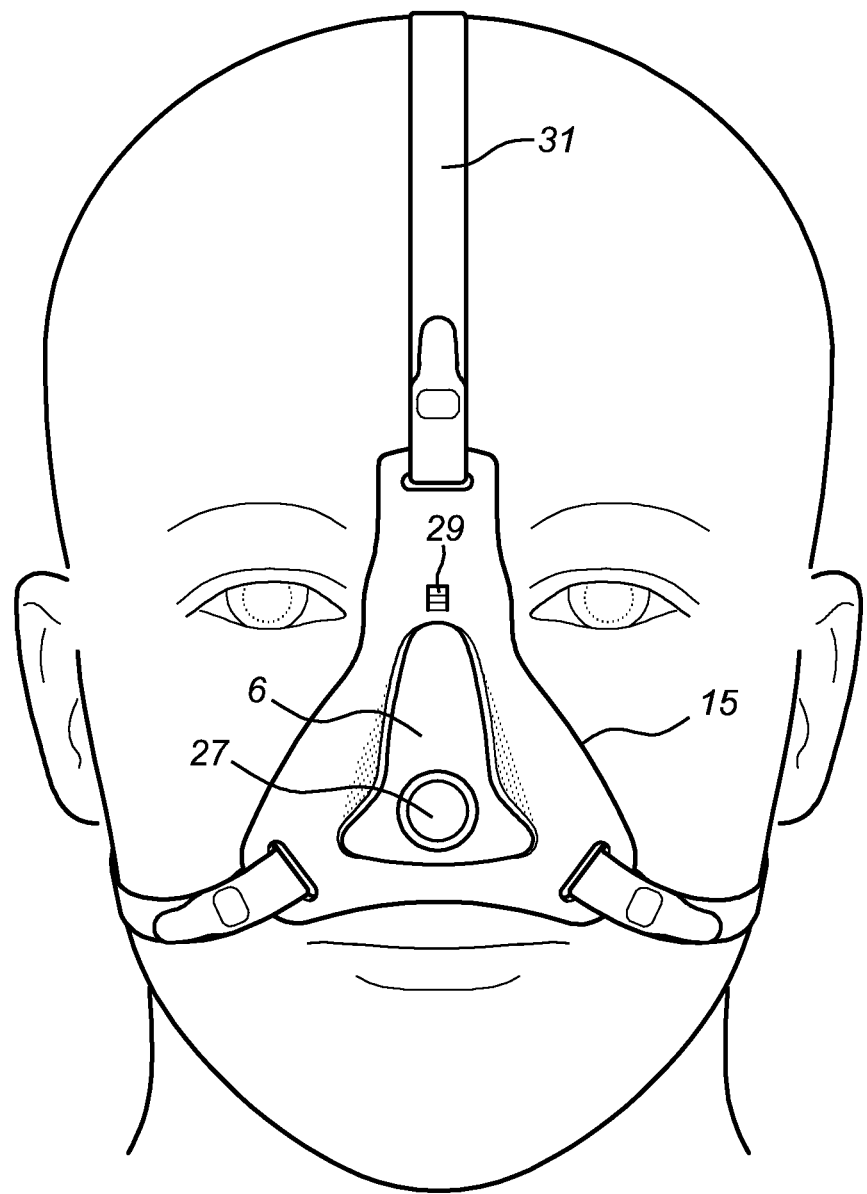
FIG. 10A shows a front view of a wearable medical support worn by a subject.

The nose mask 2 element of the support 1 is dimensioned to fit over the nose of the subject. It extends from the nose bone around at least part of the cheeks, and comprises at least one fixture 21 for a strap which passes over the back of the head. The mask 2 is disposed with an aperture 3 for the nose. The nose mask 2 may have substantially a triangular shape or may have substantially the shape of an isosceles trapezium in its molded state. As will be appreciated, the nose mask 2 may be dimensioned so as not to extend over the eyes, mouth or ears. The mask 2 is devoid of apertures for the eyes, mouth or ears (FIG. 2, FIG. 10A). The mask might be provided with more fixtures compared to the example shown in FIG. 10A. In said figure, 3 fixtures are shown at 3 different locations: one at the front head, one at the right cheek and one at the left cheek of a subject. It is to be understood that the mask can be provided with 2, 3, 4 or more fixtures at each location. Meaning that 2, 3, 4 or more fixtures can be provided at the front head and/or 2, 3, 4 or more fixtures can be provided at the right cheek and/or 2, 3, 4 or more fixtures can be provided at the left cheek of a subject. Multiple fixtures at each location provide better stability when the mask is worn.

It is to be understood that any other configuration of the molded mask, in which larger parts of the wearer's face are covered, is possible provided that the aperture for the nose with the above described flanking flaps is available. For instance the mask can extend such as to cover the mouth of the wearer. The mask can also be provided with an aperture dimensioned to fit the mouth of the wearer while the mask sheet extends to cover the area surrounding said mouth of the wearer. Said area comprises at least a part of the chin and le cheeks of the wearer.

Prior to molding, the nose mask 2 or the sheet of thermoplastic material may be flat, or rounded (e.g. U-shaped) to approximate to the profile of the face, more specifically the nose. After molding FIG. 2 and FIG. 10A, the mask 2 is adapted to match the facial contours of the subject, more specifically the nose contours of a subject.

Figure 10B:
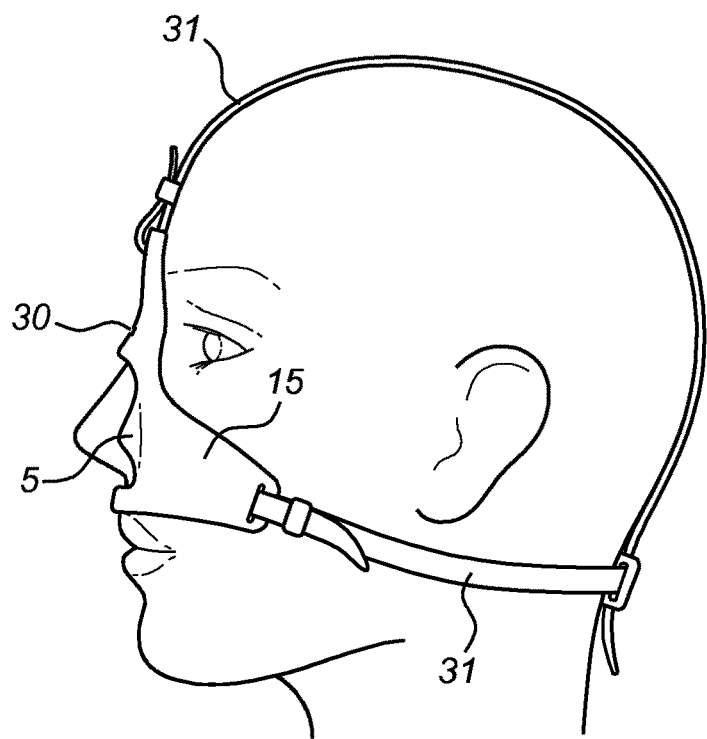
FIG. 10B shows a lateral view of a mask worn by a subject.
Figure 10C:
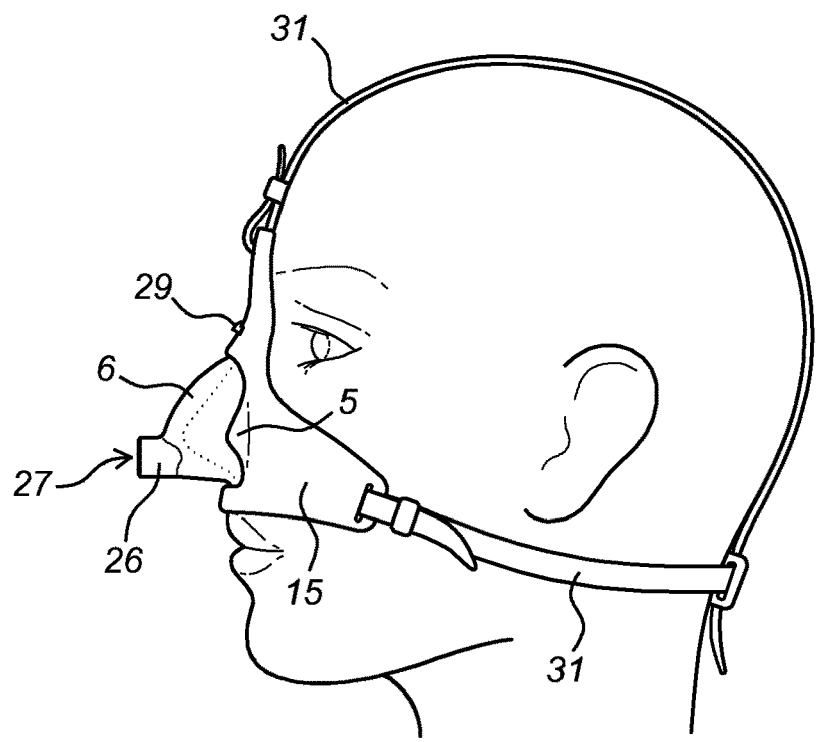
FIG. 10C shows a front view of a wearable medical support worn by a subject.
Figure 11:
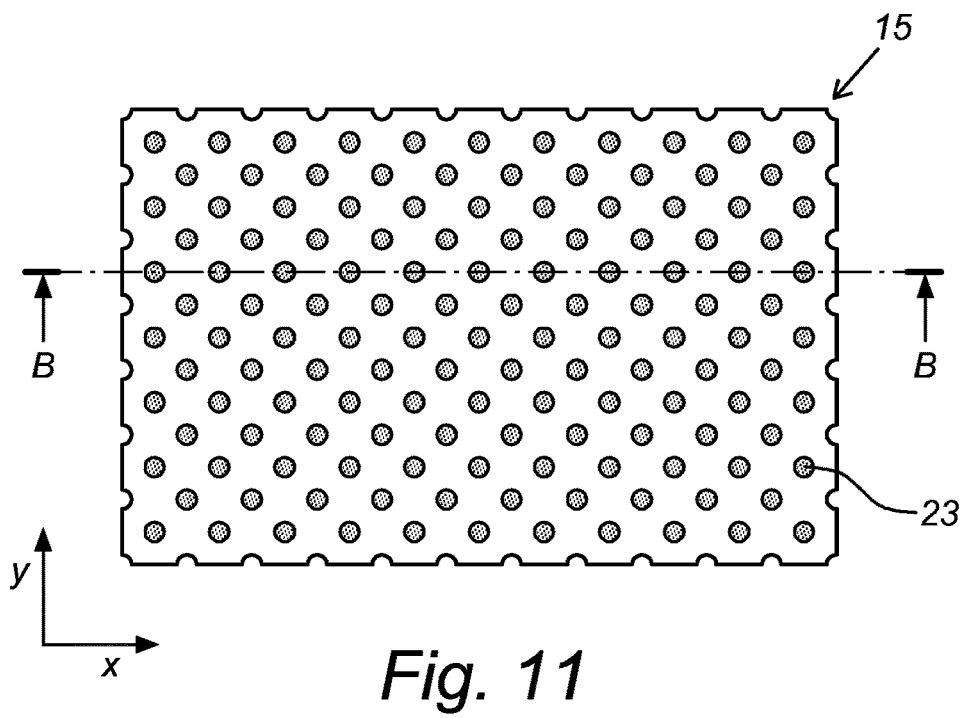
FIG. 11 shows a top view of a preferred embodiment of a thermoplastic sheet material according to the invention.

The nose mask 2 is suitable to worn by a patient as shown in FIG. 10B. The flaps 4,5 of the nose mask 2 are resting on and covering at least partially the lateral sides of the nose of the patient (FIG. 10B). The nose mask 2 might be fixed to the patient's head using straps 31 (FIG. 10B) or any other attachment means known to the person skilled in the art. The nose mask 2 can be worn by the patient with (FIG. 10C) or without the removable device 6 (FIG. 10B). FIG. 10A and FIG. 10B show the position of the flaps 4,5 when the mask is worn by a patient. Said flaps cover at least partially the lateral nose sides thereby improving the stability of the worn mask and reducing the chances of mask dislodgment.

In a preferred embodiment, the form and/or the size of the flaps 5 is variable. The form of the flaps can be triangular, rectangular, conical or any other shape. The size of each flap covers at least 10%, preferably at least 20%, more preferably at least 30%, most preferably at least 40%, even most preferably at least 50% of the lateral side of the subject's nose. The size of each flap covers at most 100%, preferably at most 90%, more preferably at most 80%, most preferably at most 70%, even most preferably at most 60% of the lateral side of the subject's nose. The size of the flaps may also be sufficient to cover the full lateral side of the nose and to extend beyond said lateral side.

The nose mask 2 element of the support 1 has a substantially a triangular shape, preferably isosceles triangular shape. With reference to FIG. 2, the mask 2 has a longitudinal length (L) and perpendicular thereto a width (W). The nose aperture 3 is preferably centrally located along the width of the nose mask 2. The nose aperture 3 may also be centrally located with respect to the longitudinal length. The nose mask 2 comprises two flaps 4, 5 flanking the nose aperture 3. Each flap is in contact with at least part of the lateral side of the nose when the mask is worn by a subject. Said flaps allow the nose bridge to be visible when the mask is worn by a subject. Each end of the triangular nose mask is disposed with a fixture 21 for a strap. The mask is configured for wearing such that the width (W) direction of the mask is oriented essentially parallel to the wearer's eye-line or his left-right axis.

The dimension of the longitudinal length (L, FIG. 2) of the nose mask 2 depends on the characteristics of the subject such as age, shape, and gender, but may be equal to or no more than 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 23 cm, 25 cm or a value in the range between any two of the aforementioned values, preferably between 10 and 18 cm.

The dimension of the width (W, FIG. 2) of the nose mask 2 may be defined as the distance between the opposing extremities of the nose mask 2. The distance is measured as presented in FIG. 2. The dimension of width (W) will depend on the characteristics of the subject such as age, shape, and gender, but may be equal to or no more than 7 cm, 8 cm, 9 cm, 10 cm, 11 cm, 12 cm, 13 cm, 14 cm, 15 cm, 16 cm, 17 cm, 18 cm, 19 cm, 20 cm or a value in the range between any two of the aforementioned values, preferably between 10 and 14 cm.

The aperture 3 for the nose is dimensioned such that the nose substantially passes there through. It is of sufficient size that at least the nostrils pass entirely through the aperture 3, for instance, during molding. It is of sufficient size that at least the nasal tip passes entirely through the aperture, for instance, during molding. Preferably, the aperture 3 of the nose mask 2 is dimensioned such that the nose bridge, the nostrils and the nose tip pass entirely there through. The aperture 3 may have substantially, partly or entirely a T shape, preferably an inverted T shape. Preferably the dimensions of the base of the inverted T shape (BT in FIG. 2) is 2 cm, 3 cm, 4 cm, 5 cm, 6 cm, 7 cm or 8 cm in length or a value in the range between any two of the aforementioned values. Preferably the height (H BT in FIG. 2) of the inverted T shape relative to the base is 2 cm, 3 cm, 4 cm, 5 cm, 6 cm, 7 cm or 8 cm in length or a value in the range between any two of the aforementioned values.

The above-mentioned dimensions are most preferably obtained when the mask is in the flattened condition, in other word measured on the sheet of heat moldable thermoplastic material. However, it will be appreciated that a curved mask can also be measured by transforming a digital model to a flattened state or by measuring along its surface.

The nose mask 2 may have a substantial triangular shape wherein at least one angle is provided with a fixture 21 for a strap 31; preferably each angle of the triangular shaped nose mask 2 is provided with at least one fixture 21 for a strap 31 as shown in FIG. 2. The substantially triangular nose mask has preferably three fixtures 21. The fixtures 21 for the strap may be a single slot, or two or more slots, however, it is not necessarily limited thereto. The fixtures 21 may comprise one part of a hook and loop fastener, or one part of a press-stud or snap-fastener, which attaches to a reciprocating element on the strap. The fixtures 21 are adapted to affix a strap that passes around the back of the head, and secures the mask 2 to the face of the subject. The strap 31 is preferably made from an elasticated substance, such as a strip of elasticated material, and may include a length adjuster, to adjust the length of the strap and thus pressure exerted by the mask 2 on the face. An example of securing the mask to the face of the subject using straps is shown in FIG. 10A. In a preferred embodiment, the straps are attached to the mask in a configuration wherein at least part of the strap is surrounding at least partially the mask sheet, for instance when both parts of a hook and loop fastener, of a press-stud or of a snap-fastener are provided on the strap itself. Said strap is introduced in the fixture and both parts of the hook and loop fastener, the press-stud or the snap-fastener are fixed to each other. This is advantageous as the pressure applied on the wearer's face is smaller compared to the pressure applied by a mask in which the straps are fixed on top and/or on the side of the mask which is not in contact with the wearer's face. In the latter case, the straps will push the mask on the wearer's face which will be uncomfortable for said wearer. In the configuration described in the frame of the present invention, the straps do not push the mask on the wearer's face but will only secure the mask to wearer's face.

In a preferred embodiment, the straps are attached to the mask in a configuration wherein at least part of the strap is surrounding at least partially the mask sheet and wherein one part of a hook and loop fastener, of a press-stud or of a snap-fastener is provided on the strap itself while the other part is provided on the mask sheet.

In a preferred embodiment, the aperture 3 of the nose mask 2 is flanked by two flaps 4, 5, as shown in FIG. 2, whereby each flap is configured to be in contact with at least part of a lateral side of the nose. Said flaps are created in the mask 2 by molding the thermoplastic sheet of the present invention directly on the face of a subject, more in particular on the nose of a subject. Said flaps are personalized as they are adapted to the specific shape of the subject's nose thereby providing good stability of the mask on the wearer's face. The mask can hence be worn during the subject's sleep with minimum risk of dislodgement. Furthermore, the pressure applied by the mask on the wearer's face will be divided over a large surface of the mask which provides a higher comfort to the wearer.

Figure 5:
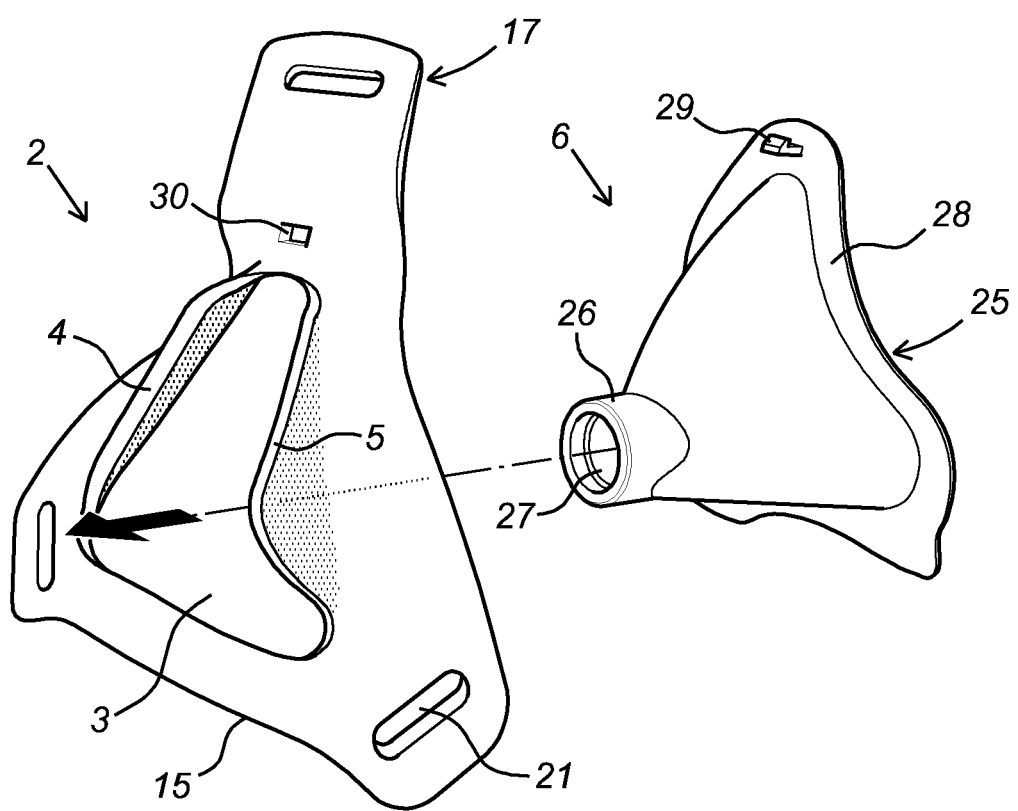
FIG. 5 shows an embodiment of coupling the nose mask shown in FIG. 2 and the device shown in FIG. 3 thereby obtaining a wearable medical support according to an embodiment of the invention.
Figure 6:
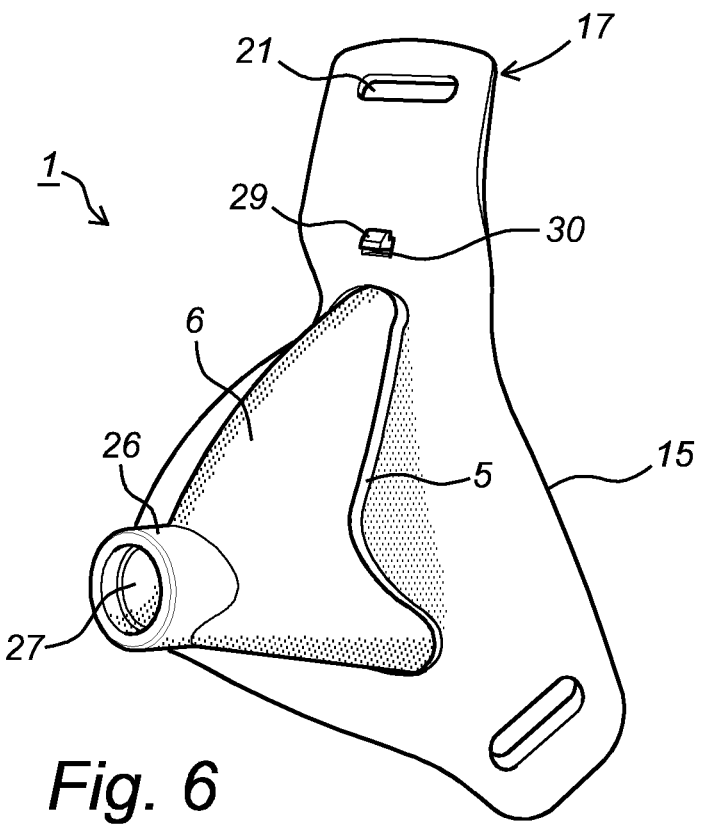
FIG. 6 is a perspective view of a wearable medical support comprising the nose mask shown in FIG. 2 and the device shown in FIG. 3.
Figure 7:
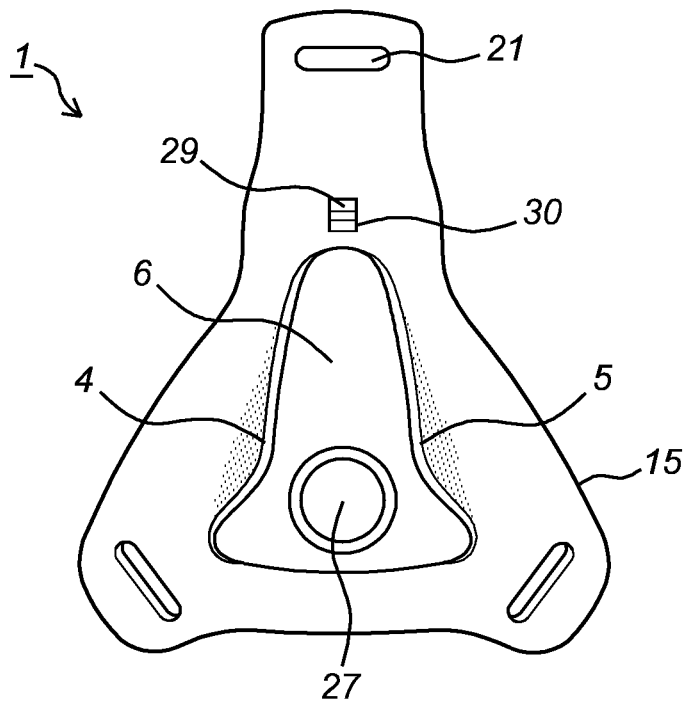
FIG. 7 is a front view of the wearable medical support shown in FIG. 6.

The wearable medical support 1 of the present invention comprises a removable device 6 (FIG. 3) configured to close fit said aperture. The device 6 is suitable and is designed to pass, at least partially, through the aperture 3 of the nose mask 2 from the skin facing surface 17 of the mask. The passage of the device through the aperture is performed by sliding the device into the aperture starting from the skin facing surface 17 of the mask towards the other surface of the mask as shown in FIG. 5. By close fit it is meant that when the device 6 in passed through the aperture 3 of the mask 2, said aperture is entirely covered or filled as shown in FIG. 6 and FIG. 7. The removable device 6 can be dismounted and replaced after regular intervals or after sufficient wear and tear, so reducing the buildup of dust and allergens; the lifespan of the wearable support 1 is thereby prolonged. Said device 6 is preferably made from a flexible material such as silicone.

Figure 4:
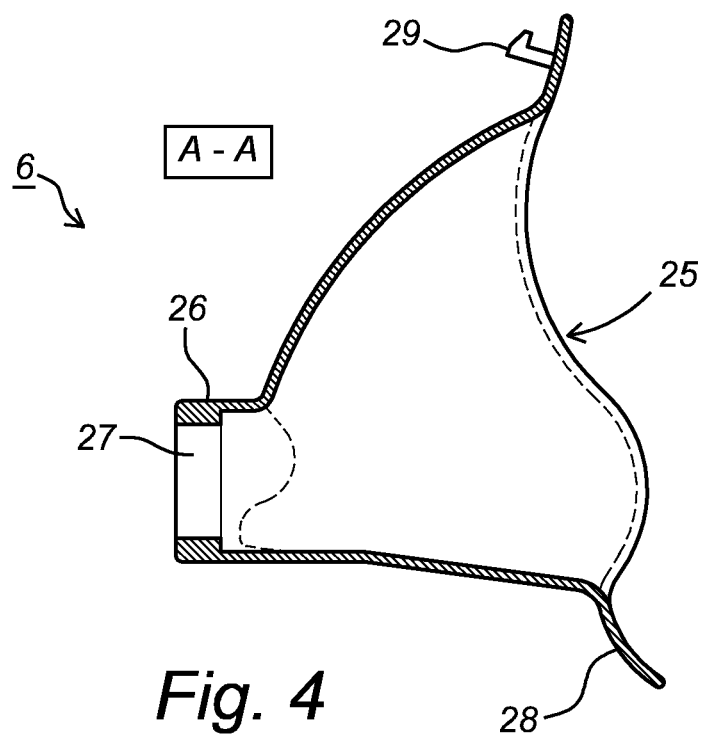
FIG. 4 shows a cross section view according to A-A of the device shown in FIG. 3.

According to one embodiment of the invention, the device 6 has a half conical or an isosceles trapezium shape. The device 6 is provided at one end with an opening 25 for receiving the nose, and at the other end with one or more couplings 7 for attaching one or more tubes for the delivery of a treatment to the nose of the subject. The coupling 7 consists of at least one tubular connection means 26 for coupling to a tube for providing a treatment. Said tubular connection means 26 has an inlet 27 through which the treatment will reach the subject's nose. It is to be understood that the opening 25 for receiving the nose is proximal to the wearer's face and that the inlet 27 of the tubular connection means 26 is distal to the wearer's face when the support is worn by a wearer (FIG. 3 and FIG. 4). The device 6 and thereby the support 1 maintains the position of the tube relative to the nose, permitting the subject to receive a treatment for prolonged periods while being able to move the head freely. The coupling 7 may be permanently or dismountably fixed to the device 6. Preferably, the coupling is permanently fixed to the device 6.

The opening 25 of the device 6 is dimensioned such as the entire nose of the subject passes there through. Hence, the device 6 is suitable to contain the complete nose of a subject. The opening 25 may be triangular, round, oblong, square of any other suitable shape. It may have the shape substantially of an isosceles triangle. The shape will be largely determined by the shape of the nose. Preferably, the opening 25 is substantially triangular in shape. It is anticipated that different sizes of the device 6 would be available to suit different sizes and shapes or nose masks, more in particular nose mask apertures 3.

In a preferred embodiment, a flange 28 is provided around the opening 25 of the device 6 (FIG. 3 and FIG. 4). The flange 28 provides a gas-sealing effect against the skin and gives a comfortable feeling to the wearer. The flange 28 of the device 6 is dimensioned to fit around the nose of the subject. As will be appreciated, the flange 28 may be dimensioned so as not to extend over the eyes, mouth or ears. The flange 28 may be planar or flat in the native state. The flange 28 is preferably oriented essentially perpendicular to the plane of the device opening 25. The flange 28 is preferably formed from any suitable material exhibiting the requisite unfoldability property i.e. the ability to be folded and unfolded without weakening or other damage. Preferably, the flange 28 is formed from the same material as the material of the device 6, most preferably silicone. The thickness of the flange 28 and of the walls of the device 6 will generally be determined by the material used for construction, and by the requisite unfoldability property i.e. the ability to be folded and unfolded without damage. However, as a general guidance, the minimum thickness of will be equal to or less than 0.5 mm, 1 mm, 2 mm, 3 mm, 4 mm, or a value in the range between any two of the aforementioned values.

In a preferred embodiment of the invention, the coupling 7 consists of a tubular connection means 26 having an inlet 27 as exemplified in (FIG. 3 and FIG. 4). The inlet 27 may be circular as shown in FIG. 3. The coupling is suitable to be connected to at least one tube for the delivery of a treatment to the nose of a subject. The coupling 7 and the device 6 are dimensioned to slidably pass through the aperture 3 of the nose mask 2 without substantial hinderance, such that the flange 28 is disposed on the skin-facing side 17 of the nose mask 2 as shown in FIG. 5, while the inlet 27 and the tubular connection means 26 are disposed on the other side of the nose mask 2, so the side of the mask which is distal from the wearer's face.

In a preferred embodiment, the device 6 and the nose mask 2 are provided with at least one snap fit attachment means. Said attachment means may comprise a protrusion 29 and an opening 30 such that the opening is clickable on said protrusion thereby dismountably attaching the device 6 to the nose mask 2 (FIG. 2 to FIG. 6). The opening can be placed on the mask 2 and the protrusion 29 on the device or vice-versa. Preferably, for the comfort of the wearer, the opening 30 is provided in the mask 2 and the protrusion 29 is provided in the device 6. In another embodiment, the device 6 might be provided with at least one protrusion (not shown) which is suitable to be attached to a corresponding receiving shape in the mask, thereby attaching said device to the mask.

In a preferred embodiment, when the support 1 is used by a subject, the skin facing surface of the flaps 4, 5 is at least partially in contact with one surface of the device 6. It is to be understood that the surface of the device which is in contact with the skin facing surface of the flaps 4, 5 is the surface which is distal from the wearer's skin when the wearable medical support is used by a subject.

The nose mask 2 is made from a thermoplastic sheet material deformable under the application of heat to conform to the contours of the face of a subject, which after cooling down retains the deformed shape and becomes rigid or semi-rigid. The nose mask comprises a thermoplastic composition containing polycaprolactone and polyurethane.

Figure 8:
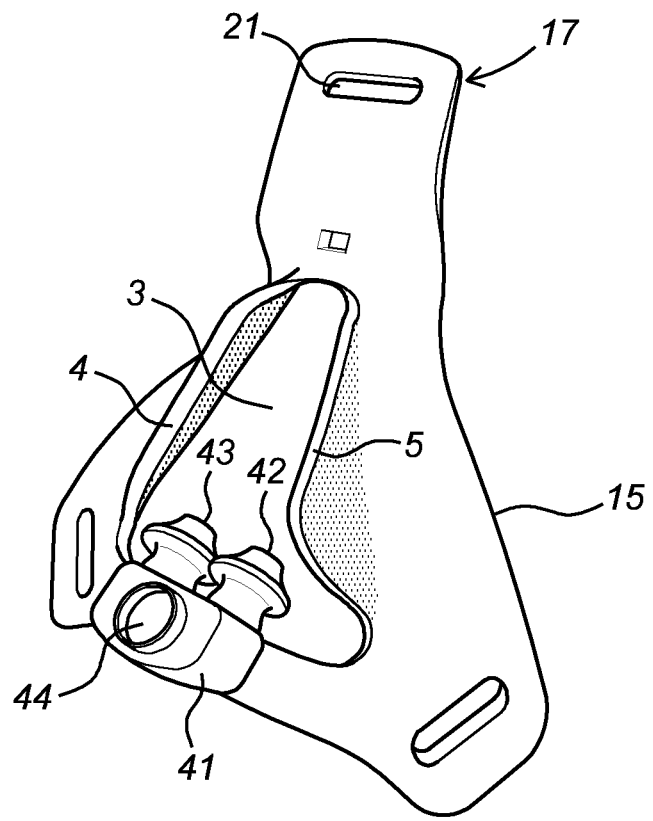
FIG. 8 is a perspective view of a wearable medical support according to another embodiment of the invention, the medical support comprising the nose mask shown in FIG. 2 and an adaptor.
Figure 9A:
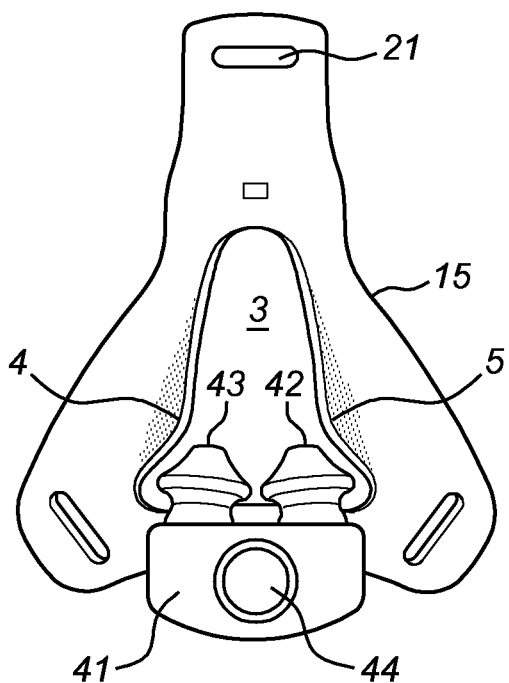
FIG. 9A is a front view of the wearable medical support shown in FIG. 6.

According to another embodiment of the invention (FIG. 8 to FIG. 9C), the treatment is delivered to the nose of a subject using a nose mask 2 as described above and an adaptor 41. Said adaptor comprises a pair of adjustable outlet nozzles 42, 43 for outlet of gas in fluid connection with an inlet port 44 for coupling to a fitting for providing gas (e.g. air). The outlet nozzles 42, 43 are positioned on the mask for entry into the nostrils. The adapter 41 may be attached to the mask 2 exterior surface using any suitable technique, such as employing adhesive, or welding methods. As shown in FIG. 8, 9A and FIG. 9C the nozzles 42, 43 are arranged in alignment with the base of the nose mask 2 aperture 3, which alignment orients the nozzles for insertion into the nose. An adapter-type coupling 41 having the above described configuration is known in the art, for instance, as a nasal pillow. Examples of manufacturers of nasal pillows include ADAM and Resmed. Typically, they have a substantially polypropylene or polycarbonate body.

Figure 9B:
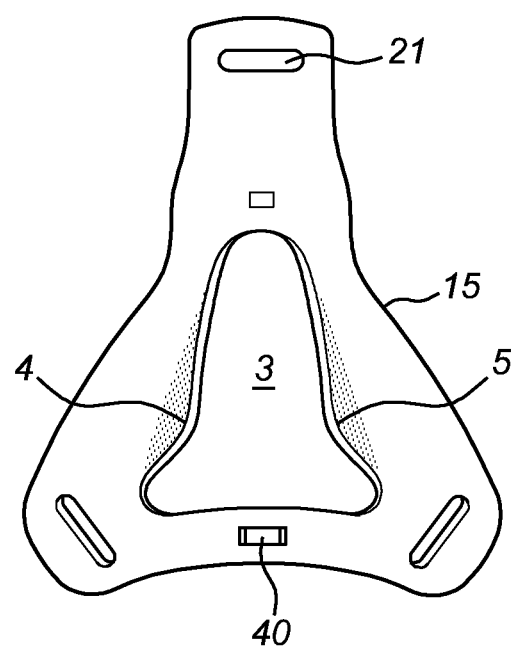
FIG. 9B is a front view of the wearable medical support shown in FIG. 6 devoid of adaptor.
Figure 9C:
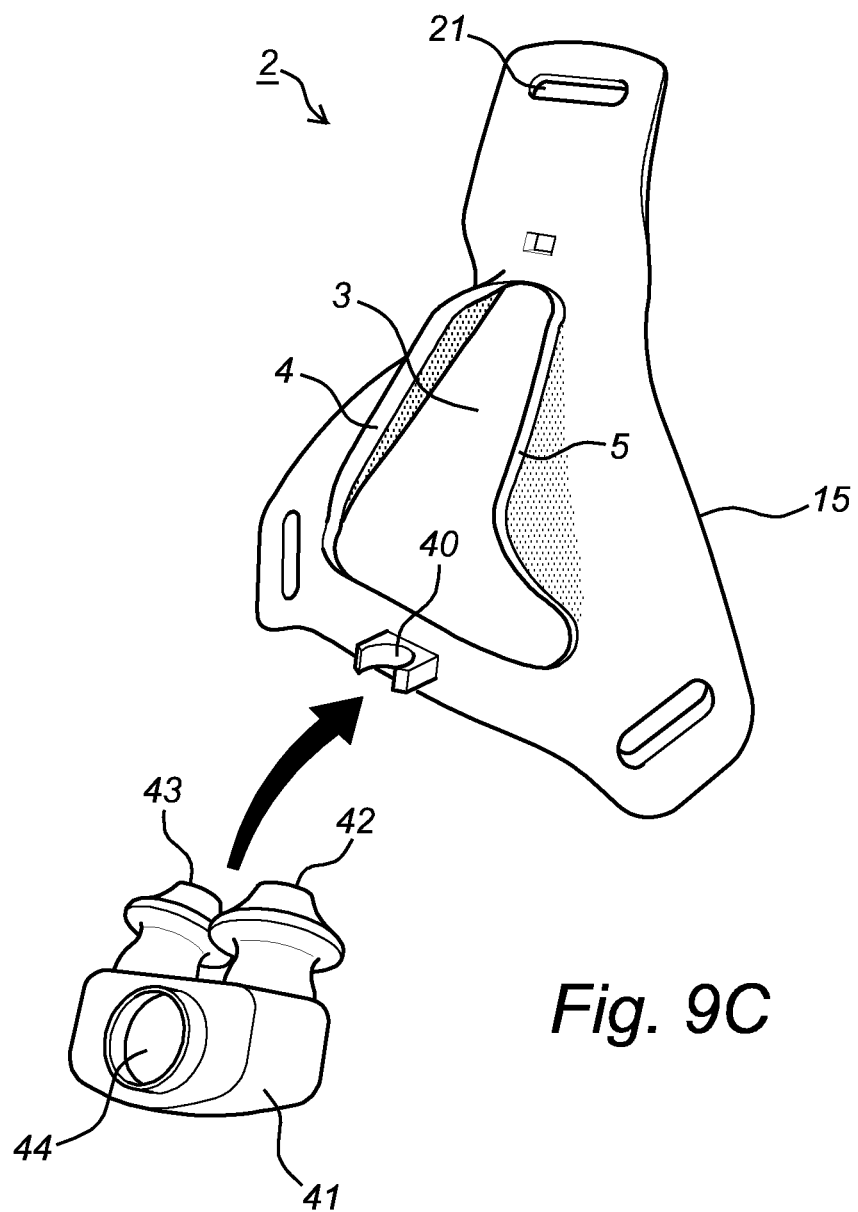
FIG. 9C shows an embodiment of coupling the nose mask shown in FIG. 2 and the adaptor thereby obtaining a wearable medical support as shown in FIG. 8.

In a preferred embodiment, a clip 40 is provided on the nose mask as shown in FIG. 9B. Said clip is configured to couple securely the adapter 41 to the nose mask and align it with the entrance to a nostril. The clip 40 is preferably formed from a non-thermoplastic material such as polycarbonate or polypropylene. FIG. 9C shows the coupling of the adaptor 41 to the nose mask 2 using a clip 40. The adapter 41 can be fixed to the nose mask by any other means such as by binding the adapter to the mask or by using a snap fit fixation means.

Figure 12:
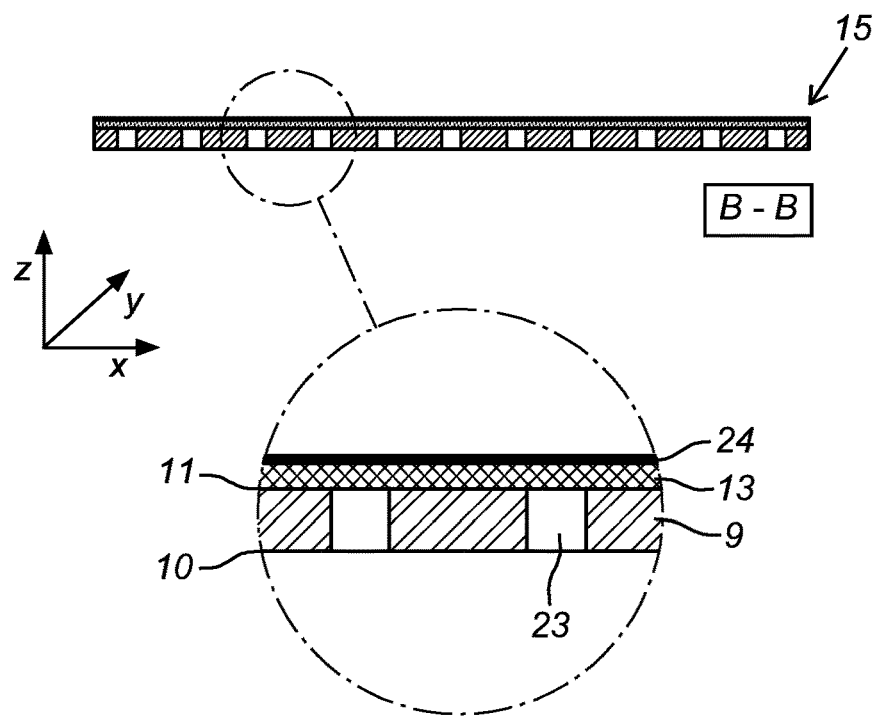
FIG. 12 illustrates a cross section B-B of a preferred embodiment of a thermoplastic sheet material bonded with a coated support layer according to the invention.
Figure 13:
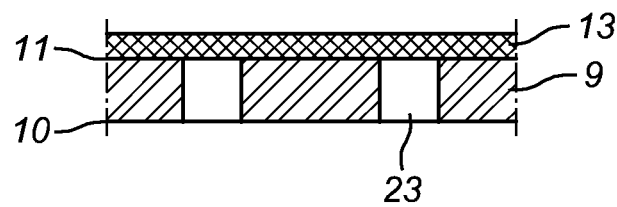
FIG. 13 depicts a cross section B-B of a preferred embodiment of a thermoplastic sheet material bonded with an uncoated support layer according to the invention.

In a preferred embodiment, the sheet of thermoplastic material 15 comprises a thermoplastic composition layer 9 having an upper surface 10 and a lower surface 11 and a support layer 13 which is bonded on the lower surface 11 of the thermoplastic composition layer 9 (FIG. 12). Said support layer can be provided with a coating 24 as shown in FIG. 12. Said support layer 13 can also be non-coated as shown in FIG. 13.

Figure 14:
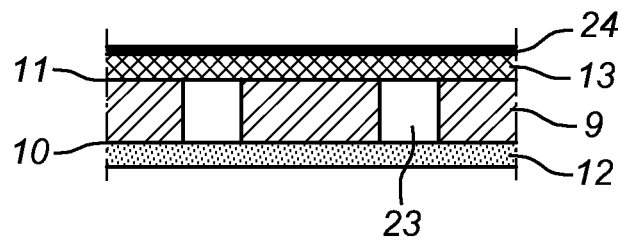
FIG. 14 illustrates a cross section B-B of a preferred embodiment of a thermoplastic sheet material bonded on one side with a coated support layer and on the other side with an elastic fabric.

In a preferred embodiment, the sheet of thermoplastic material 15 comprises a thermoplastic composition layer 9 having an upper surface 10 and a lower surface 11; a layer of elastic fabric 12; and a support layer 13. The layer of elastic fabric 12 is bonded on the upper surface 10 of the thermoplastic composition layer 9. The support layer is bonded on the lower surface 11 of the thermoplastic composition layer 9 (FIG. 14).

Figure 15:
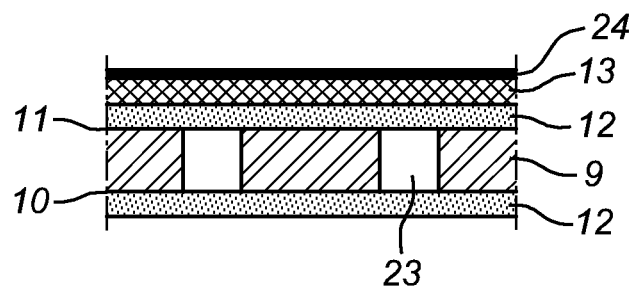
FIG. 15 illustrates a cross section B-B of a preferred embodiment of a thermoplastic sheet material bonded on both sides with an elastic fabric, the non-bonded side of one elastic fabric is further bonded to a coated support layer.

In a preferred embodiment, the sheet of thermoplastic material 15 comprises a thermoplastic composition layer 9 having an upper surface 10 and a lower surface 11; a layer of elastic fabric 12; and a support layer 13. The layer of elastic fabric 12 is bonded on the upper surface 10 and the lower surface 11 of the thermoplastic composition layer 9. The support layer is bonded on the elastic fabric 12 which is bonded on the lower surface 11 of the thermoplastic composition layer 9 (FIG. 15).

In a preferred embodiment, the sheet of thermoplastic material 15 comprises a thermoplastic composition layer 9 having an upper surface 10 and a lower surface 11; a layer of elastic fabric 12; and a support layer 13. The layer of elastic fabric 12 is bonded on the upper surface 10 of the thermoplastic composition layer 9. The support layer is bonded on the lower surface 11 of the thermoplastic composition layer 9. Preferably, a mask produced from the sheet of thermoplastic material of this embodiment is used by the wearer such as the elastic layer is not in contact with the wearer's face while the support layer is in contact with said wearer's face. Preferably, the support layer comprises a breathable foam, preferably a hydrophilic foam, more preferably a breathable hydrophilic foam, most preferably a breathable hydrophilic open cell foam. More by preference, the support layer 13 comprises a breathable hydrophilic polyurethane open cell foam suitable for continuously bonding by heat to a thermoplastic material and/or to an elastic material.

It is to be understood that the layers 9, 12 and 13 can be bonded to each other in any pattern. For instance, the thermoplastic composition layer 9 can be sandwiched between two layers of elastic fabric 12 whereby one layer of elastic fabric 12 or each of them is bonded to a layer of support fabric 13. The thermoplastic composition layer 9 can be sandwiched between two layers of support fabric 13 whereby one layer of support fabric 13 or each of them is bonded to a layer of elastic fabric 12. The thermoplastic composition layer 9 can also be sandwiched between a layer of elastic fabric 12 and a layer of support fabric 13. Any other pattern is encompassed by the present invention.

Wherein the sheet of thermoplastic material comprises a support layer, it is preferable that the mask produced from said sheet is used such as the support layer is in contact with the wearer's face.

Thermoplastic Composition Layer

By the term "thermoplastic composition layer" 9 as used herein, is understood a layer comprising a thermoplastic composition having two surfaces: an upper surface 10 and a lower surface 11. The thermoplastic composition may be chosen from the group of polycaprolactone and polyurethane or any combination thereof.

The polyurethane may be present in an amount of 0%, 10%, 20%, 30%, 40% or 50% (% by weight), preferably 20% to 40% or a value in the range between any two of the aforementioned values, most preferably 30%. The polycaprolactone may be present in an amount of 60%, 70%, 80%, or 90% (% by weight) or a value in the range between any two of the aforementioned values, preferably 60% to 80%, most preferably 70%. Typically, there will be more polycaprolactone than polyurethane which polycaprolactone lowers the temperature at which the sheet deforms. The ratio of polycaprolactone:polyurethane (weight:weight) may be 5:1, 4:1, 3:2, 3:1, 2.3:1, 2:1 preferably 2.3:1.

The molecular weight of the polyurethane may be equal to or less than 10000, 20000, 30000, 40000, 50000, 60000, 70000, 80000, 90000, 100000, 120000, 140000, 150000 or a value in the range between any two of the aforementioned values, preferably between 10000 and 100000. Polyester polyurethane is the preferred polyurethane.

The molecular weight of the polycaprolactone may be 10000, 20000, 30000, 40000, 50000, 60000, 70000, 80000, 100000, 200000, 300000, 400000, 500000 or a value in the range between any two of the aforementioned values, preferably between 10000 and 60000, more preferably between 37000 and 500000.

Caprolactone polyester polyurethane is particularly suitable, which polyurethane may be obtained by reacting isocyanate and polycaprolactone-based polyester. Such a caprolactone polyester polyurethane is commercially available as a granulate. The melting point of said polycaprolactone polyester polyurethane lies between 190° C. and 210° C. By adding the polycaprolactone, also preferably in granulate form, a thermoplastic composition is obtained that is distortable and moldable at a temperature of about 69° C. and remains distortable by cooling down about 30° C.

At this temperature, the thermoplastic composition layer 9 may be stretched at least up to twenty times the original length thereof. In the hardened condition, the thermoplastic material is rigid and has a memory effect that, after heating, returns to the shape formed on cooling. It is non-elastic in the hardened condition. The thermoplastic composition layer of the present invention is used to be directly molded on a human body part thereby obtaining anatomical shaped medical articles (corresponding to the thermoplastic composition layer at the hardened condition). The anatomical shaped medical articles obtained from thermoplastic compositions of the prior art and/or available on the market deform and return to the layer status when they are subject to heat treatment. This is not the case of the thermoplastic material of the present invention which is characterized by a memory effect. Said memory effect is very advantageous as it avoids deformation and/or a return to the layer status of the hardened thermoplastic material and hence of the anatomical shaped medical articles after certain treatments, such as sterilization and/or washing at high temperatures (from 85 to 100° C.).

The thermoplastic composition layer 9 may have a thickness of 0.8 mm, 1.0 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, 5.1 mm, 5.2 mm, 5.3 mm, 5.4 mm, 5.5 mm, 5.6 mm, 5.7 mm, 5.8 mm, 5.9 mm or 6.0 mm or a value in the range between any two of the aforementioned values.

In one embodiment, the thermoplastic composition layer 9 comprises between 1% to 40% (weight %) of microspheres of non-metallic, heat-accumulating material which is especially suited for heating in a micro-wave oven. Preferred are glass microspheres with a diameter between 20 μm and 800 μm. A coloring agent may be added to the composition.

The thermoplastic composition layer 9 is preferably provided with perforations to increase breathability. The perforations 23 may have a diameter of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm or a value in the range between any two of the aforementioned values.

A non-limiting example of a thermoplastic composition that can be used in the current invention is Turbocast® (T Tape Company BV).

Elastic Layer and Support Layer

In a preferred embodiment of the invention, the sheet of thermoplastic material 15 comprises an elastic fabric 12 bonded only on one of the surfaces 10 or 11 of the thermoplastic composition layer 9. In another embodiment of the invention, the elastic fabric 12 is bonded on both surfaces 10 and 11 of the thermoplastic composition layer 9. More by preference, the elastic fabric 12 comprises yarns that are suitable for continuously bonding by heat to a thermoplastic material.

By the term "support layer" 13 is meant a layer that comprises a different composition compared to the thermoplastic composition layer 9. In a preferred embodiment of the invention, the sheet of thermoplastic material 15 comprises a support layer 13 on one of the surfaces 10 or 11 of the thermoplastic composition layer 9. In another embodiment of the invention, the sheet of thermoplastic material 15 comprises support layers 13 on both surfaces 10 and 11 of the thermoplastic composition layer 9.

In a preferred embodiment of the invention, the support layer 13 comprises a breathable foam, preferably a hydrophilic foam, more preferably a breathable hydrophilic foam, most preferably a breathable hydrophilic open cell foam. More by preference, the support layer 13 comprises a breathable hydrophilic polyurethane open cell foam suitable for continuously bonding by heat to a thermoplastic material and/or to an elastic material.

In another preferred embodiment of the invention, the support layer 13 comprises foam, preferably a closed cell foam, more preferably a hydrophilic closed cell foam, most preferably a flexible hydrophilic foam closed cell foam.

By the term "continuously bonding" is meant that 100% of the surface area of one side of the support layer 13 and/or of the elastic fabric 12 is bonding on 100% of the surface area of one side of the thermoplastic composition layer 9.

By the term "bonding by heat" is meant that the bonding reaction is caused by heat only, no additional adhesive or glue is required.

By the term "breathable" it is meant that air can pass through the fabric and/or the material.

As used herein, the term "breathable" also refers to a material which is permeable to water vapor. Breathable fabrics of the present invention have a water vapor transmission rate WVTRs comprised between 1 and 2000 $g/m^2/$24 hours, preferably between 2 and 1800 $g/m^2/24$ hours, more preferably between 3 and 1600 $g/m^2/24$ hours, most preferably between 3 and 1400 $g/m^2/24$ hours.

By the term "breathable foam" it is meant a foam through which air passage is possible.

In a preferred embodiment of the invention, the elastic fabric 12 has an elasticity comprised between 0.5% and 100% in the x and/or y direction. More by preference, the elastic fabric has an elasticity comprised between 1% and 15% in the x and/or y direction. Most by preference, the elastic fabric has an elasticity comprised between 2% and 5% in the x and/or y direction.

The elastic fabric 12 is a flat sheet-like product which has very small height compared to the dimensions of length and width. The x and y direction are defined to be respectively the length and the width of the support layer, whereas the z direction is defined as the height.

An elasticity of 100% in the x direction means that the support layer will elongate to twice its original length upon applying an external force on said support layer and after said external force is removed, the support layer will return to its original length without loss of material properties. The term "elasticity in x direction" can be expressed as the ratio of the elongation upon application of an external force to the initial length of the material in which said force is applied. This definition holds mutatis mutandis for "elasticity in the y direction".

In one embodiment of the invention, the elasticity of the elastic fabric is equal in x and y direction. In another embodiment of the invention, the elasticity in x and y direction is different, by preference is the elasticity in y direction comprised between 20%-70% of the elasticity of the x direction. Such material will be suitable for molding a nose mask in which the deformation in x direction will be more detailed than the deformation in y direction.

By the term "elastic fabric" is meant a fabric comprising an elastic yarn or a combination of different elastic yarns. In a preferred embodiment of the invention, the elastic fabric 12 comprises a woven fabric whereby the warp and/or weft yarn are elastic thread. In another embodiment of the invention, the elastic fabric is a knitted fabric. The elastic fabric can be made according to the knowledge available in the prior art.

When the elastic fabric 12 is a knitted material, it comprises by preference a polyamide-based knitted fabric material with a thickness of between 0.05 and 1.5 mm. In one embodiment of the invention, the knitted fabric material is formed from a yarn comprising between 80% to 95% polyamide, and between 5% and 15% elastane, preferably comprising 90% polyamide and 10% elastane.

Suitable yarns for the elastic fabric of the elastic fabric 12 comprise but are not limited to: polyamide, elastane, polyester, elasticated neoprene and styrene rubber or any other elasticated material suitable for weaving or knitting.

In a preferred embodiment of the invention, the elastic fabric 12 is suitable for freely following the deformations of the thermoplastic composition layer 9, during and after molding of the sheet of thermoplastic material 15. The elastic fabric 12 will give support to the sheet of thermoplastic material 15 when it is in moldable phase but during hardening and molding of the thermoplastic composition, the elastic fabric 12 freely follows the expansions and contractions of the thermoplastic composition. When the thermoplastic composition is rigid, the elastic fabric 12 is fully adapted to the form of the sheet of thermoplastic material 15 and thereby to the form of the obtained nose mask.

In a preferred embodiment of the invention, the sheet of thermoplastic material 15 comprises a support layer 13 comprising a hydrophilic foam, preferably a hydrophilic open cell foam. More by preference, the support layer 13 comprises hydrophilic open cell foam suitable for continuously bonding to a thermoplastic material. The bonding may be heat-bonding or performed using an adequate adhesive. The hydrophilic open cell foam is selected from the group of cellular polyvinyl chloride, polyolefins, polystyrene, styrene-acrylonitrile copolymer, styrene-methylmethacrylate copolymer. Preferably, said hydrophilic open cell foam is polyurethane open-cell foam.

The density of said hydrophilic open cell foam is comprised between 1 $kg/m^3$ and 500, preferably between 10 and 450 $kg/m^3$, more preferably between 20 and 400 $kg/m^3$. The hardness of said hydrophilic open cell foam is comprised between 0.5 and 30 kPa, preferably between 1 and 25 kPa, more preferably between 1.3 and 20 kPa. The cell size of said hydrophilic open cell foam, measured by scanning electron microscopy, is comprised between 0.05 and 5 mm, preferably between 0.08 and 4 mm, more preferably between 0.1 and 3 mm. Density, hardness and cell size of the hydrophilic open cell foam can be measured by techniques known to a person skilled in the art. The hydrophilic open cell foam can be of any color, preferably the hydrophilic open cell foam have white color.

In a preferred embodiment, the elastic fabric 12 and/or the support layer 13 can be uncoated, coated and/or impregnated.

In an embodiment of the invention, the elastic fabric 12 and/or the support layer 13 is coated with a polymer. By preference, the polymer is chosen from the group comprising but not limited to elastomers such as ethylene-vinyl acetate, ethylene propylene rubber, silicone rubber; polyester, breathable polyurethane; and synthetic silicone. The elastic fabric 12 and/or the support layer 13 may be coated on one side or on both sides. The advantage of using polymer coating is that when it is applied to an elastic fabric, the coating will not alter the elastic properties of said elastic fabric. The coating will follow the expansion and contraction of the fabric freely. In a preferred embodiment of the invention, the coating of the elastic fabric 12 consists of silicone-foam, which can be made of synthetic silicone or natural silicone. Such foam has the advantage that it provides high flexibility and permeability.

In another preferred embodiment of the invention, the support layer 13, preferably hydrophilic cell foam is coated with a coating 24 consisting of silicone-foam, which can be made of synthetic silicone or natural silicone (FIG. 12, FIG. 14 and FIG. 15). The silicone-foam is breathable and has the advantage that it provides high flexibility and permeability. Moreover, when a silicone-foam is applied to a hydrophilic cell foam, the coating 24 will not alter the breathability of said hydrophilic cell foam and thereby the breathability of the sheet of thermoplastic material 15.

In another preferred embodiment of the invention, the coating 24 optionally comprises a backing layer or liner which is removed before application to the subject. The backing layer reversibly adheres to the silicone layer of the coating 24 intended for contact with the skin of the subject. Said silicone layer is sticking to the skin of the subject. The silicone layer can be a silicone pressure sensitive adhesive. The backing layer may be made of any suitable material such as, for example, polyethylene, polythene or other polymeric substance. According to an aspect of the invention, the backing layer is smooth, or is regularly patterned with pits or grooves.

In another embodiment of the invention, the elastic fabric 12 and/or the support layer 13 is impregnated. By preference, the elastic fabric 12 and/or the support layer 13 is impregnated with a polymer. More by preference, the polymer is chosen from the group comprising but not limited to elastomers such as ethylene-vinyl acetate, ethylene propylene rubber, silicone rubber; polyester; synthetic silicone.

In a preferred embodiment of the invention, the elastic fabric 12 is a silicone-coated elastic fabric whereby the silicone-coating is applied on the surface which is not bonded to the thermoplastic composition layer 9. The support layer 13 is a silicone-coated hydrophilic open cell foam whereby the silicone-coating is applied on the surface which is not bonded to the thermoplastic composition layer 9. The silicone coating can form ridges on the elastic fabric 12 and/or the support layer 13 or it can be smooth. The silicone coating can form a continuous layer or a discontinuous layer. The silicone coating can be applied in an amount of 5 g/m$^2$ to 25 g/m$^2$, preferably from 7 g/m$^2$ to 20 g/m$^2$. In another embodiment of the invention, the elastic fabric is covered with a silicone coating in an amount between 25 g/m$^2$ to 1000 g/m$^2$.

A silicone-coated elastic fabric and silicone-coated hydrophilic foam have the advantage that the silicone will act as a friction restraining material. Silicone-coated fabrics, such as textile, are known in the prior art and provide comfort to the wearer when the silicone coated side is the skin facing side of the fabric. Silicone reduces the friction between a textile and the skin. Another advantage of silicone is its heat resistance capacity; this will buffer the heat of the sheet of thermoplastic material 15 when it is directly molded on the skin. Another advantage of silicone is that it is vapor-permeable. An embodiment of the invention in which the elastic fabric 12 and/or the support layer 13 is silicone-coated is suitable to create a micro-climate where it is applied. Such micro-climate will allow for an accelerated healing of burns and or dermatologic scars and it will lessen permanent scars on the skin.

In a preferred embodiment, the present invention provides a breathable thermoplastic sheet comprising a thermoplastic composition layer 9, a support layer 13 bonded on one surface of the thermoplastic composition layer 9. The thermoplastic composition layer 9 is preferably provided with perforations 23 (FIG. 11 to FIG. 15). Said support layer 13 is preferably polyurethane open cell foam which is coated and/or impregnated with a breathable silicone elastomer. Thus, the thermoplastic sheet exhibit good breathability and improved wear comfort which is advantageous for the user.

The thickness of the support layer 13 is equal to or less than 0.025 mm, 0.05 mm, 0.06 mm, 0.08 mm, 0.1 mm, 0.5 mm, 0.8 mm, 1 mm, 1.2 mm, 1.5 mm, 2.0 mm, 2.5 mm, 3.0 mm, 3.5 mm, 4.0 mm, 4.5 mm, 5.0 mm or a value in the range between two of the aforementioned values. The thickness will depend on the thickness of hydrophilic foam, and the coating. A silicone-foam coated hydrophilic foam will have higher thickness than a non-foam coating.

In a preferred embodiment, the elastic fabric 12 is disposed on the thermoplastic composition layer 9 and bonded to it during the production process of the sheet of thermoplastic material 15. In a preferred embodiment, the elastic fabric 12 is heat-bonded to the thermoplastic composition layer 9. Said heat-bonding is performed at a temperature of 70° C.-120° C. depending on the thermoplastic composition. At this temperature, the thermoplastic composition layer 9 is melted and bonds to the elastic fabric 12 by virtue of the adhesive property of the thermoplastic composition layer 9 in its melted condition. Additional adhesives or glue can be added but are not required. Where the support layer 13 is directly bonded to the thermoplastic composition layer 9, a similar bonding method can be applied.

In a preferred embodiment of the invention, the support layer 13 is heat-bonded on the thermoplastic composition layer 3. By the term "heat-bonded" is meant that the bonding reaction is caused by heat only, no additional adhesive or glue is required.

The use of polyurethane open cell foam as a support layer 13 is advantageous as an improved thermo-fusion or heat-bonding to the thermoplastic composition layer 9 is achieved. Another advantage is a high level of comfort provided to the user as the pressure originating from the thermoplastic composition layer 9 will be better divided and thus lowered by the polyurethane open cell foam. Moreover, the obtained thermoplastic sheet material easily adheres to the forms and shapes of the body part on which it will be applied.

In a preferred embodiment of the invention, the support layer 13 is continuously bonded to the thermoplastic composition layer 9. By the term "continuously bonded" is meant that 100% of the surface area of one side of the support layer 13 is bonded on 100% of the surface area of one side of the thermoplastic composition layer 9. In another embodiment of the invention, the support layer 13 is not continuously bonded, leaving some of the surface area of the thermoplastic composition layer 9 not bonded to the support layer 13. Similarly, the elastic fabric 12 is continuously or not continuously bonded to the support layer 13.

Sheet of Thermoplastic Material

By the term "sheet of thermoplastic material" 15 as used herein, is understood a sheet of material that is deformable under the application of heat and after cooling down retains the deformed shape and becomes rigid. The overall thickness of the sheet of thermoplastic material 15 may be 1.5 mm, 1.6 mm, 1.7 mm, 1.8 mm, 1.9 mm, 2.0 mm, 2.2 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, or 4.0 mm or a value in the range between any two of the aforementioned values.

Figure 16:
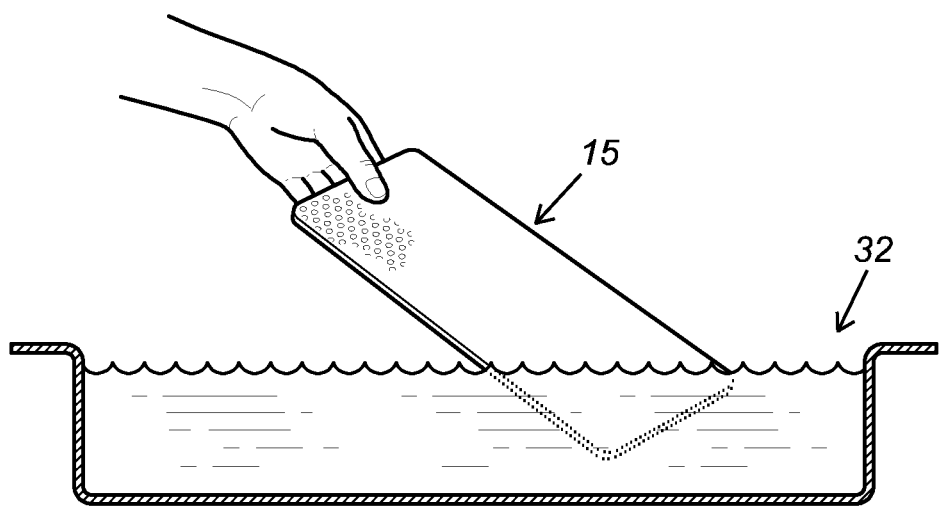
FIG. 16 depicts a preferred embodiment of the method of softening a thermoplastic sheet material according to the invention.

The sheet of thermoplastic material 15 according to the invention is by preference moldable at temperatures of between 40° C. and 90° C., more by preference between 50° C. and 70° C. This temperature is depending on the polycaprolactone content of the sheet material. The sheet material will remain in a plastic condition until it is cooled below 30° C. Typically the sheet is brought into the moldable state by heating in a water bath 32 set around 5° C. above the melting temperature, most preferable at 65° C. Such method is depicted in FIG. 16. Alternatively, the sheet of thermoplastic material 15 can be heated using a convection or fan oven, a microwave oven or a hair dryer or by any other heat producing apparatus or method.

Perforations 23 with a diameter of at least 0.5 mm and preferably between 1.0 to 2.0 mm, or a value in the range between any two of the aforementioned values may be provided in the sheet of thermoplastic material 15, so as not to hamper the skin breathing after applying the sheet.

When handling an unsupported thermoplastic sheet while it is in a moldable state, initial deformations occur in the thermoplastic composition, such as impression of fingers or gloves which make contact with the sheet. An unsupported thermoplastic sheet also deforms under its own weight when it is reheated prior to molding. A preferred embodiment of the sheet of thermoplastic material according to the invention will counteract these deformations due to the elastic properties and/or due to the additional strength provided by a coating or impregnation. As a result, a thermoplastic sheet according to the invention will keep its original form until it is molded during its plastic phase. The characteristics of the sheet of thermoplastic material will allow for wanted deformation of the thermoplastic material upon application of external forces, such as during molding.

The sheet of thermoplastic material 15 remains by preference in the moldable state for 1-10 minutes, more by preference between 2-5 minutes. The elastic fabric or the hydrophilic foam are capable of freely following the expansion and the contraction of the thermoplastic composition layer 9 while the sheet of thermoplastic material hardens during and after molding. Such sheet 15 can directly be molded on a person and is suitable for use as a brace, splint or cast material for immobilizing a part of a person. The support layer 13, preferably coated, is by preference the skin-facing side.

In a preferred embodiment of the invention, the sheet of thermoplastic material 15 comprises a Turbocast® thermoplastic composition on one surface of which a silicone-coated hydrophilic foam, preferably silicone-coated polyurethane open cell foam, is disposed. On the other surface, a silicone-coated elastic fabric is disposed. The fabric has elasticity in the y direction comprised between 20% and 70% of the elasticity in the x direction.

The sheet, according to the present invention, can directly be molded on a person and is suitable for the use as a nose mask whereby the silicone coated fabric will be the skin-facing layer. The resulting nose mask will provide a comfortable wearing and the support layer 6 prevents adhesion to the skin and/or hair by the thermoplastic composition 9. The sheet 15 exhibits excellent deformability properties, conforming to the shape of the nose without the need to apply excessive pressure. The silicone-coated support layer provides a comfortable wearing against the skin.

In an embodiment of the invention, the sheet of thermoplastic material 15 may be pre-formed prior to molding. In another embodiment of the invention, the sheet of thermoplastic material 15 is available in different standard dimensions.

A sheet of thermoplastic material 15 according to the invention is suitable to be used in the treatment of burns and/or dermatological scars. By preference, the sheet of thermoplastic material 15 comprises a coated or impregnated support layer. Said support layer is an elastic fabric or a hydrophilic foam, preferably polyurethane open cell foam. More by preference, said coating or impregnation comprises silicone. Additionally, the support layer may contain anti-bacterial products.

In another embodiment of the invention, a sheet of thermoplastic material 15 according to the invention is suitable to be used for cosmetic skincare. Additionally, the elastic fabric or the hydrophilic foam may be treated with cosmetic products, suitable to be used in cosmetic therapy. In another embodiment of the invention, a sheet of thermoplastic material 15 according to the invention is suitable to be used for treatment of dermatological scars after breast operations. A sheet of thermoplastic material 15 can be included in a bra whereby the silicone-coated/impregnated side is the skin-facing side. The inclusion of a thermoplastic sheet material according to the invention in a bra will fasten the healing process of the skin after such operation and will lessen the amount and grade of the scars.

In another aspect, the present invention provides a kit for delivery of a treatment to the nose of a subject, said kit comprises a sheet of thermoplastic material 15 for molding a nose mask 2, the sheet and the mask are as described above; a device 6 configured to close fit the aperture of the nose mask as described above; and at least one pressurizing means for applying a pressure on the sheet of thermoplastic material 15 during the molding process. In a preferred embodiment, said pressurizing means comprise binder clips or pincer shape. The pressurizing means ensure a good molding of the thermoplastic sheet and thereby an optimized fitting of the nose mask.

In another aspect, the present invention provides for the use of a kit as described above for molding directly a nose mask on a subject for delivery of a treatment to the nose of said subject.

In another aspect, the present invention provides a method for delivery of a treatment to the nose of a subject. Said method comprises the steps of heating a sheet of thermoplastic material as descried above; placing said heated sheet on a subject's nose; optionally applying a pressure on said heated sheet using pressurizing means as described above thereby obtaining, when the sheet is cooled, a nose mask as provided by the present invention; coupling the obtained nose mask to a device as described above or to an adapter also as described above; connecting said device or adapter to at least one tube through which the treatment is delivered to the nose of the subject.

Although the present invention has been described with reference to preferred embodiments thereof, many modifications and alternations may be made by a person having ordinary skill in the art without departing from the scope of this invention which is defined by the appended claims.

What is claimed is:

1. A sheet of heat moldable thermoplastic material for molding a nose mask directly on a subject's nose via thermoforming, said sheet is substantially flat and comprises one or more fixtures for attachment to a strap and a nose opening, wherein said nose opening has a substantially inverted T shape comprising a slit which is extending to a lower opening, which lower opening is substantially perpendicular to the slit, whereby the slit delimits two flanking flaps wherein said sheet is configured to, after thermoforming on the subject's nose, extend across at least part of the cheek bones of the subject, whereby the nose bridge of the subject protrudes at least partially through said slit, the nose nostrils of the subject protrude at least partially through said lower opening, and each lateral side of the nose of the subject is at least partially covered by a one of the two flanking flaps.

2. The sheet of heat moldable thermoplastic material according to claim 1, comprising a thermoplastic composition layer having an upper surface and a lower surface, a layer of elastic fabric and a support layer, wherein the layer of elastic fabric is bonded on the upper surface of the thermoplastic composition layer and the support layer is bonded on the lower surface of the thermoplastic composition layer.

3. The sheet of heat moldable thermoplastic material according to claim 2, wherein said layer of elastic fabric has similar elasticity in x direction and y direction.

4. The sheet of heat moldable thermoplastic material according to claim 2, wherein the elastic fabric is a silicon-coated elastic fabric.

5. The sheet of heat moldable thermoplastic material according to claim 2, wherein said support layer further comprises a coating on the surface which is not bonded to the thermoplastic composition layer.

6. The sheet of heat moldable thermoplastic material according to claim 2, wherein said thermoplastic composition layer is provided with perforations.

7. The sheet of heat moldable thermoplastic material according to claim 2, wherein said support layer comprises a hydrophilic foam or a closed cell foam.

8. The sheet of heat moldable thermoplastic material according to claim 7, wherein the support layer is silicone-coated.

9. The sheet of heat moldable thermoplastic material according to claim 1, whereby the sheet is moldable at a temperature between 40° C. and 90° C., and remains in plastic condition until cooled below 30° C.

10. A method for making a nose mask comprising:
(a) providing a sheet of heat moldable thermoplastic material, wherein said sheet of thermoplastic material is initially substantially flat and comprises:
(i) one or more fixtures for attachment to a strap; and
(ii) a nose opening, wherein said nose opening has a substantially inverted T shape comprising a slit which is extending to a lower opening, which lower opening is substantially perpendicular to the slit, whereby the slit delimits two flanking flaps;
(b) thermoforming said sheet of thermoplastic material directly on a subjects nose to form the nose mask, wherein the nose mask after said thermoforming is configured to extend across at least part of the cheek bones of the subject, and wherein the nose bridge of the subject protrudes at least partially through said slit, and wherein the nose nostrils of the subject protrude at least partially through said lower opening; and each lateral side of the nose of the subject is at least partially covered by one of the two flanking flaps.

11. The method according to claim 10, further comprising molding the sheet of thermoplastic material at a temperature between 50° C. and 70° C., wherein the thermoplastic material remains in plastic condition until cooled below 30° C.

12. The method according to claim 10, wherein said sheet of thermoplastic material comprises a thermoplastic composition layer having an upper surface and a lower surface, a layer of elastic fabric and a support layer, and wherein the layer of elastic fabric is bonded on the upper surface of the thermoplastic composition layer and the support layer is bonded on the lower surface of the thermoplastic composition layer.

13. The method according to claim 12, wherein said layer of elastic fabric has similar elasticity in x direction and y direction.

14. The method according to claim 12, wherein the elastic fabric is silicon-coated.

15. The method according to claim 12, wherein said support layer comprises a hydrophilic foam or a closed cell foam.

16. The method according to claim 15, wherein the support layer is silicone-coated.

17. The sheet of heat moldable thermoplastic material according to claim 1, wherein the sheet is moldable at a temperature between 50° C. and 70° C., and remains in plastic condition until cooled below 30° C.

* * * * *